United States Patent [19]

Beare et al.

[11] 3,991,179

[45] Nov. 9, 1976

[54] INFLUENZA VACCINES

[76] Inventors: Abraham Sestel Beare, Flat 2B, Harvard Hospital, Coombe Road, Salisbury, Wiltshire; David Arthur John Tyrrell, .29 The Ridgeway, Stanmore, Middlesex; David McCahon, 10. Bullswater Common, Pirbright, near Woking, Surrey, all of England

[22] Filed: Nov. 29, 1974

[21] Appl. No.: 528,555

[30] Foreign Application Priority Data

Nov. 29, 1973 United Kingdom.............. 55469/73

[52] U.S. Cl................................... 424/89; 195/1.1; 195/1.2; 195/1.3

[51] Int. Cl.$^{2}$.................... A61K 39/18; C12K 5/00; C12K 7/00

[58] Field of Search ................ 424/89; 195/1.1, 1.2, 195/1.3

[56] References Cited
OTHER PUBLICATIONS

Kilbourne, Science, vol. 160 (Apr. 1968) pp. 74 & 75.

Beare et al. – The Lancet, Dec. 11, 1971, pp. 1271–1273.

Kilbourne, Hospital Practice, Oct. 1971, pp. 103–106, 111, 112 and 114.

*Primary Examiner*—Sam Rosen
*Attorney, Agent, or Firm*—Donald Brown

[57] ABSTRACT

A recombinant influenza virus strain derived from (a) an over-attenuated influenza A strain which has been passaged solely in chicken egg cultures, manifests a relatively high yield of virus in such cultures and has an increased capacity for plaque formation on calf kidney cells and (b) a virulent influenza A strain which manifests a relatively low culture yield of virus and is substantially free from contaminating mammalian viruses; a method of manufacturing the recombinant strain and a vaccine incorporating it.

The virulent strain is preferably one fairly recently isolated at the time of manufacture of the vaccine. The over-attenuated strain should have sufficient antigenic distinction between it and the virulent strain and have a proven safety record.

16 Claims, No Drawings

INFLUENZA VACCINES

The present invention relates to influenza vaccines and in particular to recombinant influenza vaccines derived from two different virus strains, and to their method of manufacture.

Influenza is a virus disease of the upper respiratory tract which manifests itself in the form of fever, headache, sore-throat, muscular pain and fatigue. Unlike any virus diseases, influenza confers only temporary specific immunity in a subject and thus the disease may be contacted repeatedly whenever an epidemic occurs. In recent years therefore influenza vaccination has been carried out to confer active immunity against a prevailing strain of influenza virus and hence to prevent or restrict contraction of influenza during epidemics.

In the 1940s inactivated influenza vaccines were successfully employed to reduce markedly the incidence of the disease but such vaccines suffer from the disadvantage that the killed virus cannot multiply in the host. A relatively high amount of inoculum is therefore required and a correspondingly large quantity of antigenic material has to be manufactured, tested and distributed. The problem is particularly acute for influenza vaccines since the time required for their manufacture may well prevent their availability until after an epidemic has passed even if manufacture is commenced in immediate response to the outbreak. Moreover the unpredictability of some antigenic variation of any future influenza strain limits the value of advance manufacture and storage on a large scale, and requires quick adaptation to new epidemics spreading across the world.

Live attenuated influenza vaccines were therefore proposed in which the virus strain has been passaged in a variety of cell systems until its ability to produce disease is lost whilst its immunogenic character is fully retained. Once inoculated into the host the virus multiplies to some extent so that only a small initial inoculum is required with consequent savings in time and labour in production. For these vaccines, however, it is important that the attenuated strains are innocuous and that infection of susceptible contacts is minimal.

Genetic recombination between various influenza strains to provide improved antigenic material with advantageous characteristics of each strain for use in inactivated or live vaccines is already known. For instance hybrid strains derived from an attenuated and a virulent strain have been described and tested but none of the recombinant variants obtained has been acceptable for practical purposes. It was thought to be advantageous to use an influenza strain attenuated by passages on a variety of cell systems, including that of various mammals, but the properties of the resulting strains are considered unsuitable for safety reasons in view of the history of this attenuated parent strain.

It has now been found that satisfactory and acceptable recombinant influenza strains can be prepared from the combination of an "over-attenuated" influenza A parent strain, particularly the A-2 type, with a virulent influenza A parent strain, the recombinant strains selected having the growth characteristics of the over-attenuated strain coupled with the antigenic properties of the virulent strain. The over-attenuated strain used is one which has been passaged solely in chicken egg cultures and manifests a relatively high yield of virus in chicken eggs and an increased capacity for plaque formation on calf kidney cells. The virulent influenza A strain on the other hand manifests a relatively low culture yield of virus, whilst being substantially free from contaminating mammalian viruses.

The "over-attenuation" required for the first strain means that the number of passages for attenuation has been substantially greater than what is normally necessary for the removal of pathogenicity. The attenuated viral component retains its antigenicity, however, after these numerous passages, i.e. both its haemagglutinin (H) antigen and its neuraminidase (N) antigen, so that its immunogenic ability is not impaired. Such strains produce practically no symptoms or side effects when administered to sensitive subjects, such as children, and would be expected to have a satisfactory safety record based on appropriate testing. It may be preferred to use a strain, e.g. an A-2 strain, which was isolated 10 or even 20 years ago in order that there may be sufficient antigenic distinction between this and the recent virulent strain and that the safety of the strain can be firmly established. Indeed there should be a differential of at least 1 unit between the haemagglutinin antibody types of the two parent strains e.g. $H_2$ and $H_3$, the higher number corresponding to the more recent virulent strain.

Such attenuated strains can for instance be obtained by egg passaging as described in the specification of Japanese Pat. No. 310,662. This specification discloses in particular the production of the A/OKUDA/57($H_2N_2$) strain which was derived from an A-2 type strain isolated in Osaka, Japan during the 1957 epidemic and attenuated according to the method therein described, and in addition discloses another A-2 type strain, the A/KINUGASA/57 strain. A further strain which may be suitable is the A2/JAPAN/305/57 strain which is deposited in the American Type Culture Collection (ATCC) under number VR-100.

The Okuda strain which is the preferred attenuated virus strain for use in the present invention may alternatively be obtained from the World Health Organisation, World Influenza Centre, National Institute of Medical Research, Mill Hill where this strain, passaged to the 280th egg passage level, is deposited and to be made publicly available.

The other strain required for recombination according to the present invention may be selected from a number of A type influenza virus strains which have retained their virulence in man and have been cultured only in egg or other cultures approved by the control authorities, for example the National Institute for Biological Standards, Holly Hill, Hampstead. It is preferred however that the strain is one fairly recently isolated at the time of manufacture of the recombinant vaccine. The likelihood of the vaccine providing the required immunity against infection with a future strain will then be correspondingly enhanced in view of the antigenic similarity between these strains.

For instance at the priority date of the present application a virulent strain which has been applied successfully is the A/ENGLAND/42/72($H_3N_2$) virus. More recently the A/FINLAND/4/74($H_3N_2$) virus has been isolated and found to be particularly suitable for incorporation in a recombinant influenza vaccine. Both these strains have been deposited at the above international organisation at the National Institute of Medical Research at Mill Hill and are now publicly available.

According to the present invention therefore there is provided in one aspect a recombinant influenza virus strain derived from (a) an over-attenuated influenza A strain, preferably an A-2 strain, such as the A/OKUDA/57 strain, which has been passaged solely in chicken egg cultures, manifests a relatively high yield of virus in such cultures and has an increased capacity for plaque formation on calf kidney cells and (b) a virulent influenza A strain which manifests a relatively low culture yield of virus and is substantially free from contaminating mammalian viruses.

Before recombination of the virulent and the attenuated strains it may be advisable in some circumstances for them to undergo cloning so that each strain is derived from a single original virus particle. Moreover it is usual for deposited strains to be available in lyophilised form and thus as a further preliminary each virus strain must in this instance be reconstituted in a suitable medium such as phosphate buffered saline and tryptose phosphate broth, desirably in the presence of antibiotics to kill any bacteria which may be present. After inoculation into the allantoic sac of eggs, desirably specific pathogen free (SPF) eggs, and incubation the allantoic fluid may be extracted and stored until required at a low temperature.

In order for the two strains to recombine satisfactorily it is necessary that the differential between their virus yielding capacities in chicken eggs is not too large. The high yielding attenuated virus is therefore irradiated with ultraviolet light or gamma radiation, or alternatively is heated to produce approximately 99% inactivation of the total virus infectivity and hence bring its yield capacity in line with that of the relatively low yielding virulent virus strain. This and the subsequent recombination process wherein the samples of the virus strains are allowed to grow together in a single egg culture, is disclosed in Postgraduate Medical Journal (1973) 49, 195–199.

It should be pointed out that the same virus strains when made to recombine on the same type of cells under identical conditions but in separate cultures may not recombine in a completely reproducible manner and slight differences in properties, for example in virus yielding capacity, may occur. However there are a very limited number of possible recombinations, and reasonable trial or experiment can produce a virus strain which meets the requirements of the present invention. If the preferred Okuda strain is used as the attenuated parent virus strain, it has been found, advantageously, that nearly all possible recombinants are suitable for the practice of the invention.

In accordance with the preferred method used for the manufacture of the recombinants of the present invention, the attenuated parent strain is irradiated with ultraviolet light and then recombined with the virulent parent strain by simultaneous inoculation into allantois-on-shell (AOS) cultures derived from 10-day-old SPF eggs. After incubation, to each culture is added a hyperimmune serum, preferably rabbit or ferret serum, prepared against a highly purified virus whose haemagglutinin is antigenically closely related to or identical with the attenuated parent strain. By this means the virus yield of the attenuated parent strain can be reduced such that very little of the parent strain remains after the recombination. Since the virus yielding capacity of the virulent parent strain is relatively low, there is no need to suppress this virus in the same way.

Those cultures showing haemagglutination after further incubation are harvested and portions withdrawn for haemagglutinin and neuraminidase inhibition tests, for selection of those recombinants having the antigenic composition of the virulent influenza A parent strain, and hence potentially useful in vaccines. The cultures so selected are then taken and cloned to remove residual parent viruses and those recombinants found from the above not to be suitable for further testing are discarded. The cloning is carried out by the limit dilution method as described in Postgraduate Medical Journal (vide supra). Each selected recombinant strain may then be passaged in a suitable egg culture, such as SPF eggs or AOS cultures derived therefrom, for about one or two passages to increase its yield and a sterile, antibiotic-free stock prepared in SPF eggs for testing in volunteers. These tests are so designed to check that the recombinant strain is genetically stable and capable of immunising when inoculated into man.

In another aspect of the present invention, therefore, there is provided a method of manufacturing a recombinant influenza strain as hereinbefore defined which comprises the steps of inactivating the parent overattenuated strain to substantially reduce its original infectivity, inoculating this strain together with the parent virulent strains into a single culture, incubating the culture and then cloning it to remove parental strains and isolating the desired recombinant strain. Conveniently suppression of the parent attenuated strain may be achieved by addition of an appropriate hyperimmune serum to the culture. Suitable recombinants may then be selected by testing the cultures so obtained for haemagglutination and antigenic character by routine procedures and the desired recombinant isolated by cloning.

The sterile stock prepared from the selected recombinant strain is reisolated from volunteers, for example by intranasal administration and collection of the nasal washings. The virus seed so obtained may then be repassaged, preferably twice, in egg cultures and a vaccine prepared therefrom in a diluent such as phosphate buffered saline in the presence of stabilisers, preferably hydrolysed gelatin and sorbitol. The resulting vaccine, which may be freeze-dried and then reconstituted when required, may then be administered to humans, advantageously by the intranasal route.

In further aspects of the present invention therefore there is provided a vaccine comprising a recombinant influenza strain as hereinbefore defined, and a method of manufacturing the vaccine.

The invention will now be described with reference to the following Examples but is in no way to be considered limited by the same.

EXAMPLE 1

Recombinant of A/OKUDA/57($H_2N_2$) with A/ENGLAND/42/72 ($H_2N_2$)

(i) Preparation of Parent Strains (a) Attenuated Virus Strain - A/OKUDA/57($H_2N_2$)

The Okuda A-2 strain, which has been passaged solely in egg cultures and given to tens of thousands of children in Japan in aerosol form without untoward effects, was obtained at the 280th passage level, having a haemagglutinin titre of 1:1280, in a lyophilised form. This was reconstituted in 1.5 ml of a mixture of phosphate buffered saline and 10% tryptose broth and 1500 international units each of penicillin and streptomycin, inoculated into the allantoic sac of three 10-day-old SPF eggs and incubated at 35° C for 3 days. The allantoic fluid from one egg was selected and stored in small volumes at −60° C. For the recombination experiment a small aliquot was thawed and diluted 1:100 in normal saline and irradiated with ultraviolet light for 30 seconds, which was sufficient to produce approximately 99% inactivation of the total virus infectivity.

(b) Virulent Virus Strain - A/ENGLAND/42/73($H_3H_2$)

This strain was received as a lyophilised sample of allantoic fluid via Dr. G. C. Schild of the National Institute of Medical Research, Mill Hill. The virus strain was an egg isolate which had been passaged three times in eggs and had a haemagglutinin titre of 1:128. The lyophilised material was reconstituted in a mixture of phosphate buffered saline and 10% tryptose phosphate broth and 1000 international units each of penicillin and streptomycin. 0.2 ml of this was inoculated into the allantoic sac of three 10-day-old SPF eggs and incubated at 35° C for 3 days. The allantoic fluid from one egg was selected and stored in small volumes at −60° C.

(ii) Recombination and Isolation of Recombinants

AOS cultures were prepared from 10-day-old SPF eggs and dispensed into the wells of a haemagglutination tray. 0.03 ml of each virus was then added to each culture : the A Okuda strain being diluted 1:100 before the irradiation and the live A England strain being diluted 1:30 in normal saline. The tray was placed in a plastic bag and incubated on a shaker (approx. 100 oscillations/minute) at 37° C. After 4 hours incubation hyperimmune rabbit serum was added to each well to a final dilution of 1:3000 in order to suppress the growth of the attenuated parent strain and the incubation was continued. This serum, which was prepared against highly purified A/SINGAPORE/57($H_2N_2$) virus strain which is very closely antigenically related to the Okuda strain, was diluted one hundred fold in normal saline prior to use, and exposed under an ultraviolet lamp for 2 minutes as an extra precaution to destroy any extraneous agents that might be present. After a total of 48 hours incubation at 37° C a 5% suspension of red blood cells from SPF chickens was added to each well to a final concentration of 0.5%. 22 out of 77 cultures showed haemagglutination and were harvested individually as presumptive recombinants. 0.1 ml of each presumptive recombinant was inoculated into 10-day-old SPF eggs which were incubated at 37° C for 3 days. At the end of this time the eggs were examined for the presence of haemagglutinin and the type of haemagglutinin was identified in haemagglutinin inhibition tests. In this preliminary test four isolates were identified as showing high virus yielding capacity and the haemagglutinin component of the virulent A England strain as required. One of these was subsequently rejected as neuraminidase inhibition tests showed that this recombinant had the neuraminidase component of the parent attenuated A Okuda strain and not of the desired virulent A England strain.

Each remaining harvest of those AOS cultures so selected was then cloned three times to remove residual parent viruses and those recombinants which were found in the above test not to be suitable for submitting to the clinical testing stage. As a preliminary the virus culture was disaggregated by treatment in an ultrasonic bath (input 80 kilocycles/second) for 30 seconds. The cloning was then effected by diluting the culture in 2-fold or 3-fold steps and then inoculating into 10-day-old embryonated eggs or AOS cultures, using a minimum of eight replicate cultures for each dilution. The limit dilution clones were isolated from cultures in which the virus dilution used infected only approximately 10% of the replicates, as indicated by positive haemagglutination when tested with red blood cells from SPF chickens. Each selected clone was then passaged once or twice in 9–12-day-old SPF eggs and a sterile stock of each selected recominant prepared in 10-day-old SPF eggs (without the use of antibiotics). This stock was then examined by haemagglutinin and neuramidase inhibition tests to check its antigenic composition and if suitable submitted for clinical testing.

EXAMPLE 2

Recombinant of A/OKUDA/57($H_2N_2$) with A/FINLAND/4/74($H_3N_2$)

(i) Preparation of Parent Strains (a) Attenuated Virus Strain - A/OKUDA/57($H_2N_2$)

A small aliquot of the allantoic fluid inoculated with the Okuda strain from Example (i) (a) was thawed and cloned twice in SPF eggs. It was then diluted 1:100 in normal saline and irradiated with ultraviolet light for 30 seconds.

(b) Virulent Virus Strain - A/FINLAND/4/74($H_3N_2$)

This strain was isolated in eggs from a throat swab provided by Dr. Cantell at the Central Public Health Laboratory, Helsinki, Finland and had a haemagglutinin titre of 1:2560. The virus strain had thus been passaged once in man and once in SPF eggs and was then cloned twice in these eggs. The allantoic fluid from one egg was selected and stored in small volumes at −60° C.

(ii) Recombination and Isolation of Recombinants

The A Okuda parent strain was mixed with the A Finland strain at 1:30 dilution as AOS cultures in a haemagglutination tray, and the tray was incubated in a plastic bag on a shaker at 36° C. After 1 hour, antiserum was added to each well to a final dilution of 1:2000 in order to suppress the growth of the attenuated parent strain and the incubation was continued. The antiserum was a hyperimmune ferret serum prepared against A/OKUDA/57 and was irradiated before use by exposure at 1:20 dilution to an ultraviolet lamp for 2 minutes. After a total of 31 hours incubation a 0.5% suspension of red blood cells from SPF chickens was added to each well to detect haemagglutinating activity. 19 out of 64 cultures showed haemagglutination, and these were harvested individually. 0.1 ml of each presumptive recombinant was inoculated into SPF eggs which were incubated at 37° C for 3 days. The eggs were then examined for the type of haemagglutinin by haemagglutinin inhibition tests, for infectivity in AOS cultures and for haemagglutinin titre in eggs. On the basis of these results 11 of the 19 harvested cultures were cloned twice in AOS cultures and once in SPF eggs according to the method described in Example 1(ii). A sterile antibiotic-free stock of each selected recombinant was prepared in 10-day-old SPF eggs and the stocks examined to check the antigenic composition. 8 of these had the antigens of A/FINLAND/4/74 and 3 of these were similar to A/OKUDA/57 in their growth properties and were those chosen for submission for clinical testing.

Clinical Trials

Clinical trials were carried out using the three selected recombinant strains under reference numbers WRL 55, 65 and 68 from Example 1 and the three strains WRL 94, 100 and 105 from Example 2, the respective virus yielding capacities being shown in Tables 1 and 2 respectively.

The virus strain selected was passaged once in chicken eggs and diluted to an appropriate titre. 1.0 ml amounts of this virus were then given intranasally to each of a number of volunteers. Nasal washings were collected on the third and fourth days after virus inoculation and were inoculated into the allantoic cavity of 11-day-embryonated hens' eggs. These were tested for virus haemagglutinin after 2 days' incubation at 33° C. Sera collected before the trial and 14 days after inoculation were assayed for haemagglutination-inhibiting (HAI) antibodies by standard methods as, for example, described in Br. Med. J 1968, iv, 36, 385.

In Tables 3 and 4 the following data is shown: the recombinant virus strain used, the infectivity dose in the $E.I.D._{50}$ of the virus inoculum, the number of volunteers, the initial HAI titre in the serum, the reactions (as indicated by incidence and duration of pyrexia, coryza and subjective discomfort, and on increased use of handkerchiefs), the fraction of volunteers exhibiting excretion of virus in the nasal washings 3 and 4 days after inoculation and that fraction whose serum showed (a) a rise in HAI titre (b) a substantial rise in HAI titre i.e. at least a 4-fold rise.

Further experiments were conducted to assess the genetic stability of the recombinant strains. For example the first nasal washing of a volunteer inoculated with WRL 55 recombinant strain was diluted 1:5 and given intranasally to 5 volunteers. The results showed that WRL 55 is excreted in very small amounts indeed. Experiments were also conducted with WRL 105 and 100 in which the recombinant was reisolated from the nasal washing of a subject previously inoculated with triple cloned recombinant and then passaged in SPF eggs to prepare a large vaccine harvest. This harvest could then be tested in a larger number of volunteers and the genetic stability of the recombinant strain established. It will be seen that WRL 105 has a greater genetic stability than WRL 100 and is hence preferred.

TABLE 1

| VIRUS STRAIN | | ANTIGENS | | VIRUS YIELDING CAPACITY (HAU/0.25ml) |
|---|---|---|---|---|
| | | HAEMAGGLUTININ | NEURAMINIDASE | |
| PARENT VIRUS STRAINS | A/OKUDA/57 | $H_2$ | $N_2(1957)$ | 1000 |
| | A/ENGLAND/42/72 | $H_3$ | $N_2(1972)$ | 96 |
| RECOMBINANT VIRUS STRAINS | WRL 55 | $H_3$ | $N_2(1972)$ | 256 |
| | WRL 68 | $H_3$ | $N_2(1972)$ | 512 |
| | WRL 68 | $H_3$ | $N_2(1972)$ | 512 |

HAU = Haemagglutinin units.

TABLE 2

| VIRUS STRAIN | | ANTIGENS | | VIRUS YIELDING CAPACITY (HAU/0.25ml) |
|---|---|---|---|---|
| | | HAEMAGGLUTININ | NEURAMIDIDASE | |
| PARENT VIRUS STRAINS | A/OKUDA/57 | $H_2$ | $N_2(1957)$ | 941 |
| | A/FINLAND/4/74 | $H_3$ | $N_2(1974)$ | 445 |
| RECOMBINANT VIRUS STRAINS | WRL 105 | $H_3$ | $N_2(1974)$ | 920 |
| | WRL 100 | $H_3$ | $N_2(1974)$ | 1080 |
| | WRL 94 | $H_3$ | $N_2(1974)$ | 993 |

HAU = Haemagglutinin units.

TABLE 3

| TRIAL | RECOMBINANT VIRUS STRAIN | INFECT.$^y$ DOSE $E.I.D_{50}$/ml | NO. OF VOLUNTEERS | INITIAL HAI TITRE IN SERUM | | REACTIONS | Excretion of Virus 3rd day | 4th day | RISE IN HAI TITRE | 4 FOLD RISE IN HAI TITRE |
|---|---|---|---|---|---|---|---|---|---|---|
| | | | | 24 | 24 | | | | | |
| 1 | WRL 55 | $10^{7.5}$ | 5 / 7−1 \ 1 | 5 1 0 | 0 0 1 | 5 nil 1 mild 1 moderate | 1/5 1/1 0/1 | 0/5 1/1 0/1 | 5/5 1/1 0/1 | 5/3 1/1 0/1 |
| 2 | WRL 55 | $10^{7.5}$ | 8 | 7 | 1 | 8 nil | 4/8 | 4/8 | 8/8 | 7/8 |
| 3 | WRL 55 | $10^{6.5}$ | 4 | 2 | 2 | 4 nil | 1/4 | 1/4 | 1/4 | 1/4 |
| 4 | WRL 55 | $10^{5.5}$ | 2 / 3 \ 1 | 3 | 0 | 2 nil 1 moderate | 0/2 0/1 | 0/2 0/1 | 1/2 1/1 | 1/2 1/1 |
| 5 | WRL 65 | $10^{6.5}$ | 11 / 13 \ 2 | 3 1 | 8 1 | 11 nil 2 mild | 1/11 2/2 | 1/11 2/2 | 7/11 2/2 | 4/11 2/2 |
| 6 | WRL 68 | $10^{7.6}$ | 3 | 2 | 1 | 3 nil | 0/3 | 0/3 | 2/3 | 1/3 |

TABLE 3-continued

| Trial | Recombinant Virus Strain | Infect' Dose E.I.D$_{50}$/ml | No. of Volunteers | Initial HAI Titre in Serum <24 | Initial HAI Titre in Serum >24 | Reactions | Excretion of Virus 3rd day | Excretion of Virus 4th day | Rise in HAI Titre | 4 Fold Rise in HAI Titre |
|---|---|---|---|---|---|---|---|---|---|---|
| 7 | WRL 68 | $10^{7.6}$ | 5 / 9–3 \ 1 | 1 1 1 | 4 2 0 | 5 nil 3 mild 1 moderate | 2/5 1/3 0/1 | 3/5 1/3 0/1 | 3/5 2/3 1/1 | 2/5 1/3 0/1 |

TABLE 4

| Trial | Recombinant Virus Strain$^a$ | Infect$^v$ Dose EID$_{50}$/ml | No. of Volunteers | Initial HAI Titre in Serum <24 | Initial HAI Titre in Serum >24 | Reactions | Excretion of Virus 3rd day | Excretion of Virus 4th day | Rise in HAI Titre | >4 Fold Rise in HAI Titre |
|---|---|---|---|---|---|---|---|---|---|---|
| 1 | WRL 105 aaa/1 | 7.0 | 4 / 7 | 4 | — | 3 nil 1 mild$^b$ | 1/3 1/1 | 1/3 1/1 | 3/3 1/1 | 1/3 0/1 |
| 2 | WRL 105/1/74 | 7.5 | 3 / 9 \ 15 \ 6 | 9 | 3 — 6 | 3 v.mild 5 v.mild 1 mild 2 moderate 1 NS | 2/3 0/5 0/1 1/2 0/1 | 2/3 0/5 0/1 1/2 1/1 | 3/3 3/4* 1/1 2/2 0/1 | 2/3 2/4* 1/1 2/2 0/1 |
|  |  |  |  |  | 6 | 3 nil 2 v.mild 1 NS | 0/3 1/2 0/1 | 0/3 1/2 0/1 | 2/3 2/2 1/1 | 1/3 2/2 0/1 |
| 3 | WRL 100 aaa/1 | 7.3 | 3 / 5 | 3 | — | 2 nil 1 v.mild | 0/2 1/1 | 0/2 1/1$^b$ | 2/2 1/1 | 1/2 1/1 |
| 4 | WRL 100/1/74 | 7.3 | 2 / 8 \ 18 \ 10 | 8 | 2 — 10 | 2 nil 1 nil 1 v.mild 2 mild 4 severe | 0/2 0/1 0/1 2/2 4/4 | 0/2 0/1 0/1 2/2 4/4 | 1/2 1/1 0/1 2/2 4/4 | 1/2 1/1 0/1 2/2 4/4 |
|  |  |  |  |  | 10 | 3 nil 3 v.mild 1 mild 1 moderate 2 severe | 1/3 3/3 1/1 1/1 2/2 | 0/3 1/3 1/1 1/1 2/2 | 3/3 3/3 1/1 1/1 2/2 | 1/3 2/3 0/1 1/1 2/2 |
| 5 | WRL 94 aa/1 | 7.0 | 1 / 14 \ 13 | 1 | — 13 | 0 nil 8 nil 5 V.mild | 0/1 1/8 1/5 | 0/1 1/8 0/5 | 0/1 6/8 4/5 | 0/1 4/8 4/5 |

$^a$WRL 105 aaa/1 Triple cloned isolate of recombinant
WRL 105/1/74 Recombinant reisolated from nasal wash of b, and passaged in SPF eggs to produce vaccine stock.
*1 post-inoculation serum sample not available
NS not suitable for grading.
WRL 100 aaa/1: Triple cloned isolate of recombinant.
WRL 100/1/74: Recombinant WRL 100 aaa/1 reisolated from nasal wash of b., and passaged twice in SPF eggs to produce vaccine stock. Vaccine inoculated directly without further passage.
WRL 94 aa/1: Double cloned isolate of recombinant

What we claim is:

1. A method of manufacturing a recombinant influenza virus strain derived from (a) an over-attenuated influenza A parent strain selected from the group consisting of A/OKUDA/57($H_2N_2$), A/KINUGASA/57 and A$_2$/JAPAN/305/57 which has been passaged solely in chicken egg cultures, manifests a relatively high yield of virus in said cultures and has an increased capacity for plaque formation on calf kidney cells and (b) a virulent influenza A parent strain which manifests a relatively low culture yield of virus and is substantially free from contaminating mammalian viruses which comprises the steps of inactivating the parent over-attenuated strain which has been passaged solely in chicken egg cultures, manifests a relatively high yield of virus in such cultures and has an increased capacity for plaque formation on calf kidney cells to substantially reduce its original infectivity, inoculating this strain together with the parent virulent strain into a single culture, incubating the culture, cloning it to remove parental strains and selecting the desired recombinant strains by haemagglutination and neuraminidase inhibition tests.

2. A method as claimed in claim 1, in which the over-attenuated strain is inactivated by irradiation with ultraviolet light or gamma radiation or by heating.

3. A method as claimed in claim 1, which comprises the addition of a hyperimmune serum, prepared against a virus antigenically closely related or identical to the over-attenuated strain, during the incubation to suppress this parent strain.

4. A method as claimed in claim 3, in which the hyperimmune serum is diluted in normal saline and irradiated with ultraviolet light to remove contamination.

5. A method as claimed in claim 3, in which the hyperimmune serum is rabbit or ferret serum.

6. A method as claimed in claim 1, in which a presumptive recombinant is detected by haemagglutination on addition of red blood cells from chickens to the culture.

7. A method as claimed in claim 6, in which the recombinant having the desired antigenic character is selected out by haemagglutinin and neuraminidase inhibition tests.

8. A method as claimed in claim 1 in which the virus culture is ultrasonically treated prior to cloning.

9. A method as claimed in claim 1, in which the culture is cloned by the limit dilution method.

10. A method as claimed in claim 1, in which the selected clone is further passaged in eggs.

11. The method of claim 1 in which the parent over-attenuated strain is inactivated to the degree necessary in order to bring its yield capacity in line with that of the relatively low yield virulent virus strain.

12. The method of claim 10 in which the parent over-attenuated virus is inactivated to produce approximately 99% inactivation.

13. The recombinant virus strain manufactured by the process of claim 1 in a vaccine carrier.

14. The recombinant virus strain as claimed in claim 13 wherein the attenuated parent strain is A/OKUDA/57 ($H_2N_2$) in a vaccine carrier.

15. The recombinant virus strain as claimed in claim 14 wherein the virulent strain is A/ENGLAND/42/72 ($H_3N_2$) in a vaccine carrier.

16. The recombinant virus strain as claimed in claim 14 wherein the virulent strain is A/FINLAND/4/74 ($H_3N_2$) in a vaccine carrier.

* * * * *